(12) United States Patent
Wu et al.

(10) Patent No.: US 7,557,237 B2
(45) Date of Patent: Jul. 7, 2009

(54) PROCESS FOR THE SYNTHESIS OF 3-(3-FLUORO-4-HYDROXYPHENYL)-7-HYDROXYNAPHTHONITRILE

(75) Inventors: Yanzhong Wu, Bronx, NY (US); Jianxin Ren, Nanuet, NY (US); Mousumi Ghosh, Elmwood Park, NJ (US); Mahmut Levent, Bloomfield, NJ (US); Karen W. Sutherland, New City, NY (US); Panolil Raveendranath, Monroe, NY (US)

(73) Assignee: Wyeth, Madison, NJ (US)

(*) Notice: Subject to any disclaimer, the term of this patent is extended or adjusted under 35 U.S.C. 154(b) by 692 days.

(21) Appl. No.: 10/933,184

(22) Filed: Sep. 1, 2004

(65) Prior Publication Data

US 2005/0054870 A1    Mar. 10, 2005

Related U.S. Application Data

(60) Provisional application No. 60/501,700, filed on Sep. 9, 2003.

(51) Int. Cl.
    C07C 255/03    (2006.01)
(52) U.S. Cl. .................................... 558/424
(58) Field of Classification Search ................. 558/424
    See application file for complete search history.

(56) References Cited

U.S. PATENT DOCUMENTS

| 5,554,621 A | 9/1996 | Poindexter et al. |
| 2003/0181519 A1 | 9/2003 | Mewshaw et al. |

FOREIGN PATENT DOCUMENTS

| WO | WO 98/11040 A1 | 3/1998 |
| WO | WO 98/50334 A1 | 11/1998 |
| WO | WO 03/051805 A | 6/2003 |

OTHER PUBLICATIONS

Triflate from Wikipedia.*
Suzuki reaction from Wikipedia.*
Kloubert et al., A Direct and Efficient Synthetic Method for Nitriles from Ketones, Synthetic Communications (2000), vol. 30, (16), pp. 2873-2887.
Pryde et al., Synthesis of 2-Tetralones via a Novel 1,2-Carbonyl Transposition of 1-Tetralones, Tetrahedron Letters (1996), vol. 37, No. 19, pp. 3243-3246.
Meyer et al., Structure-Activity Studies for a Novel Series of N-(Arylethyl)-N-(1,2,3,4-tetrahydronaphthalen-1-ylmethyl)-N-methylamines Possessing Dual 5-HT Uptake Inhibiting and α₂-Antagonistic Activities, Journal of Medicinal Chemistry, Mar. 28, 1997, vol. 40, No. 7, pp. 1049-1062.
Tolbert et al., Photoexcited Proton Transfer from Enhanced Photoacids, Journal American Chem. Soc., (1994), 116, pp. 10593-10600.
Hayashi et al, Preparation and Binding Affinity of New Porphyrin Host Molecule for Ubiquinone Analogues, Chemistry Letters, (1994), pp. 1749-1752.
Thummel et al., Aromatization of 1,4-Dihydrobenzocycloalkenes, 1,4-Dihydronaphthocycloalkenes, and Related Systems, J. Org. Chem., (1980), 45, pp. 1633-1637.
Radtke et al., Zum Ablauf der Dehydrierung von Dihydroarenen durch Chinone, Chem. Ber. 123 (1990) pp. 627-633.
Moore et al., Preparation of 1-Ethynyl-7-Methoxynaphthalene, OPPI Briefs, vol. 21, No. 3, (1989), pp. 386-388.
Gant et al., Oxazoline-Mediated Synthesis of the *Gossypium* Sesquiterpene Lacinilene C-7 Methyl Ether and a Structually Related HIV-1 Reverse-Transcriptase Inhibitor, Tetrahedron Letters (1993), vol. 34, No. 23, pp. 3707-3710.
Murphy et al., Synthesis and Characterization of Iodobenzamide Analogues: Potential D-2 Dopamine Receptor Imaging Agents, J. Med. Chem. (1990), vol. 33, No. 1., pp. 171-178.
Miller et al., Formation and Rearrangement of 8a-Benzyl-2-*tert*-butyl-1(8a*H*)-naphthalenone, a Ketone with a Ring System Consisting Entirely of Fused Blocked Aromatic Rings, J. Org. Chem. (1987), 52, pp. 3390-3394.
Fries: Schimmelschmidt; JLACBF; Justus Liebigs Ann. Chem. (1930), 484; pp. 245 & 271.
Nielsen et al., The Suzuki Reaction Under Solvent-Free Conditions, Synthetic Communications (2000), vol. 30(19), pp. 3501-3509.
Brooks et al., Boron Trichloride/Tetra-*n*-Butylammonium Iodide: A Mild, Selective Combination Reagent for the Cleavage of Primary Alkyl Aryl Ethers, J. Org. Chem. (1999), 64, pp. 9719-9721.

* cited by examiner

*Primary Examiner*—James O Wilson
*Assistant Examiner*—Ebenezer Sackey
(74) *Attorney, Agent, or Firm*—Pepper Hamilton LLP

(57) ABSTRACT

A process for making a compound of formula I

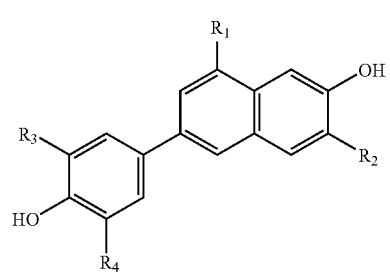

and intermediate compounds thereof, wherein $R_1$ is CN, F or Cl; $R_2$ is H or Br; and $R_3$ and $R_4$ are each independently H or F. The compounds of formula I are useful in the treatment of chronic inflammatory diseases, such as rheumatoid arthritis.

10 Claims, No Drawings

PROCESS FOR THE SYNTHESIS OF 3-(3-FLUORO-4-HYDROXYPHENYL)-7-HYDROXYNAPHTHONITRILE

This application claims priority from provisional application(s) No. 60/501,700 filed on Sep. 9, 2003.

FIELD OF THE INVENTION

This invention relates to a process for the production of 3-(3-fluoro-4-hydroxyphenyl)-7-hydroxynaphthonitrile, a selective ligand of estrogen receptor-beta, and related analogue and intermediate compounds.

BACKGROUND OF THE INVENTION

Estrogens affect many organ systems, and consequently can play a role in a number of conditions or disease states. Estrogen receptors are ligand-activated transcription factors and belong to the nuclear hormone receptor superfamily which includes progesterone, androgen, glucocorticoid and mineralocorticoid receptors. Upon binding ligand, these receptors dimerize and can activate gene transcription either by directly binding to specific DNA sequences or interacting with other transcription factors. A class of proteins can also interact with the receptors and modulate their transcription activity.

The most potent endogenous estrogen is 17β-estradiol, and the activity of this estrogen can be mimicked or blocked by many compounds. Some compounds can have mixed activity, acting as an agonist in one tissue and an antagonist elsewhere; these are called selective estrogen receptor modulators, and are potentially useful therapeutic agents. The discovery of such therapeutically useful compounds and efficient methods for making them is an important goal in the pharmaceutical industry.

According to David C. Pryde, et al., *Synthesis of 2-Tetralones Via A Novel 1,2-Carbonyl Transposition of 1-Tetralones*, Tetrahedron Lett. (1996), 37(19), 3243-3246, α-tetralones A may be converted to nitriles B by reaction with trimethyl-SiCN in the presence of a $ZnI_2$ catalyst followed by the addition of $POCl_3$ and pyridine:

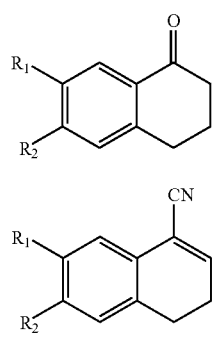

The following multi-step conversion of 7-methoxy-1-tetralone to 7-methoxy-1-naphthonitrile has been described by T. Hayashi, et al., *Preparation And Binding Affinity of New Porphyrin Host Molecule for Ubiquinone Analogs*, Chem. Lett. (1994), (9), 1749-52:

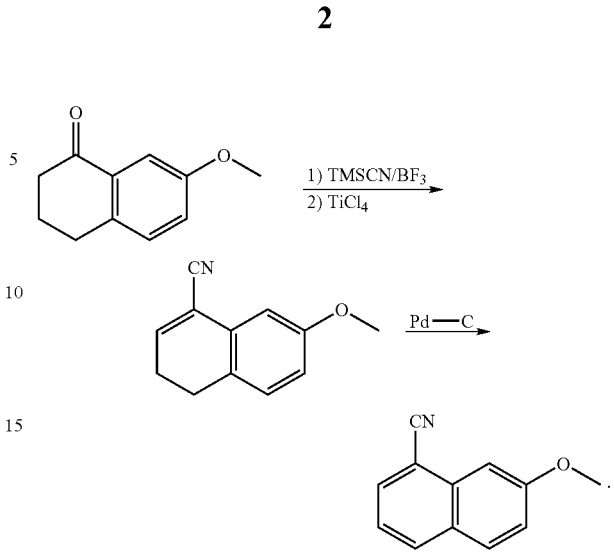

The coupling reaction of diverse aryl halides with phenylboronic acid under solvent-free conditions has been reported using Pd(PPh3)4 catalyst under ball-milling conditions. Inert NaCl was added to the reaction mixtures to make them sufficiently powdery. The order of reactivity was complementary to the normal Suzuki reaction. S. F. Nielsen, et al., *The Suzuki Reaction Under Solvent-Free Conditions*, Den. Synthetic Communications (2000), 30(19), 3501-3509.

SUMMARY OF THE INVENTION

The present invention comprises a process for making a compound of formula I

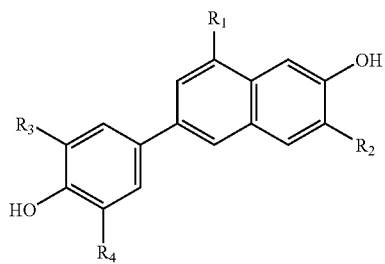

wherein
$R_1$ is CN, F or Cl;
$R_2$ is H or Br;
and $R_3$ and $R_4$ are each independently H or F,
said process comprising the following reaction steps:

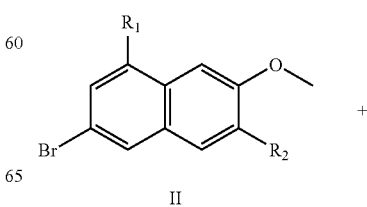

-continued

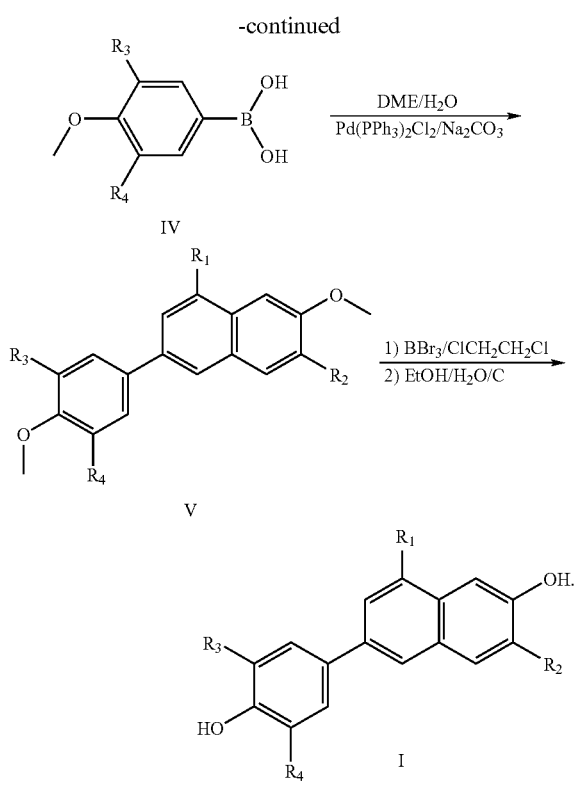

Preferably, $R_1$ is CN, $R_2$ is H, $R_3$ is F and/or $R_4$ is H.

The invention further comprises a method for making the compound of formula II in which $R_1$ is CN and $R_2$ is H, comprising heating the compound of formula III

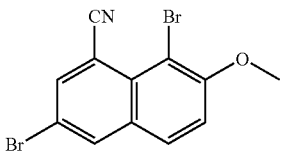

with stannous chloride in a mixture of acetic acid and concentrated hydrochloric acid.

Preferably, this process is performed at a temperature of approximately 100° C.

The invention also provides the novel compound of formula III and a process for making same by dibrominating 7-methoxy-1-naphthonitrile using approximately 2-6 equivalents of bromine in acetic acid at a temperature of approximately 40-70° C., preferably at about 65° C.; sodium bisulfite may be added at the end of the reaction to reduce excess bromine. A novel process for making 7-methoxy-1-naphthonitrile is also provided, which comprises:

a) mixing a solution of 7-methoxy-1-tetralone and zinc iodide with trimethylsilyl cyanide to form a reaction mixture, preferably in toluene solvent at about 60° C.;

b) adding phosphorus oxychloride and pyridine to the reaction mixture, preferably refluxing for about 6-9 hours, to form an unsaturated nitrile; and, c) reacting the unsaturated nitrile with 2,3-dichloro-5,6-dicyano-1,4-benzoquinone, preferably in toluene at about 60° C., to produce the 7-methoxy-1-naphthonitrile.

Various objects and advantages of the invention will be apparent to those skilled in the art from the description below and the appended claims.

DETAILED DESCRIPTION OF THE PREFERRED EMBODIMENTS

In a highly preferred aspect of this invention illustrated in Scheme 1, there is provided a new and improved process for the large-scale production of 3-(3-fluoro-4-hydroxyphenyl)-7-hydroxy-1-naphthonitrile (1). Commercial material 3,4-dihydro-7-methoxy-1(2H)-naphthalenone (7-methoxy-1-tetralone) may be transformed into an unsaturated nitrile (3) as shown on Scheme 1. The reaction is performed in toluene solution. Upon the completion of the reaction, it is quenched by caustic solution. The reaction mixture is extracted with toluene. After washing the toluene solution, the crude unsaturated nitrile (3) is aromatized directly in this toluene solution by stirring with 2,3-dichloro-5,6-dicyano-1,4-benzoquinone (DDQ) at 60° C. for 2 h. The solid is removed by filtration and the filtrate is washed with sodium hydroxide solution and brine and respectively. Most of the solvent is removed by distillation and heptane is added to precipitate the product. 7-methoxy-1-naphthonitrile (4) is isolated. The expected yield over these two steps is at least 70-75%. By performing two reactions in the same solvent, isolation of the low melting point intermediate (3) can be avoided, improving efficiency and yield.

Bromination of 7-methoxy-1-naphthonitrile (4) with bromine in acetic acid is a very temperature sensitive reaction. The compound 8-bromo-7-methoxy-1-naphthonitrile is produced rapidly at room temperature with two equivalent of bromine. It produces many poly-brominated impurities when the temperature is above 70° C. In this process of the present invention, 7-methoxy-1-naphthonitrile (4) is di-brominated at 40-70° C. with 2-6 equivalents of bromine in acetic acid. Upon the completion of the reaction, the reaction mixture is quenched with excess sodium bisulfite to reduce excess bromine and the product precipitates and is isolated with an expected yield on the order of 90-95% with high purity. This dibromide, without further purification, is heated with stannous chloride in a mixture of acetic acid and concentrated HCl at 100° C. The bromine in 8 position is selectively reduced. The product, 3-bromo-7-methoxy-1-naphthonitrile (6) is filtered from the reaction mixture after the reaction is complete. Typically, the yield is 70-80% over 2 steps with 95%+HPLC purity.

In a highly preferred process of this invention, 3-Bromo-7-methoxy-1-naphthonitrile (6) is coupled with 3-fluoro-4-methoxyphenylboronic acid, which is commercially available, under the well-known Suzuki condition using sodium bicarbonate and catalytic amount of dichloro-bis(triphenylphosphine) palladium (II) in a mixture of water and 1,2-dimethoxyethane to give 3-(3-fluoro-4-methoxyphenyl)-7-meythoxy-1-naphthonitrile (8); typically the yield is approximately 98% with about 95%+HPLC purity. Finally, in this highly preferred process 3-(3-fluoro-4-methoxyphenyl)-7-methoxy-1-naphthonitrile (8) is demethylated using boron tribromide at about 83° C. and recrystallized from a mixture of water and ethanol to give 3-(3-fluoro-4-hydroxyphenyl)-7-hydroxy-1-naphthonitrile (1), typically in about 73% yield with 99%+HPLC purity.

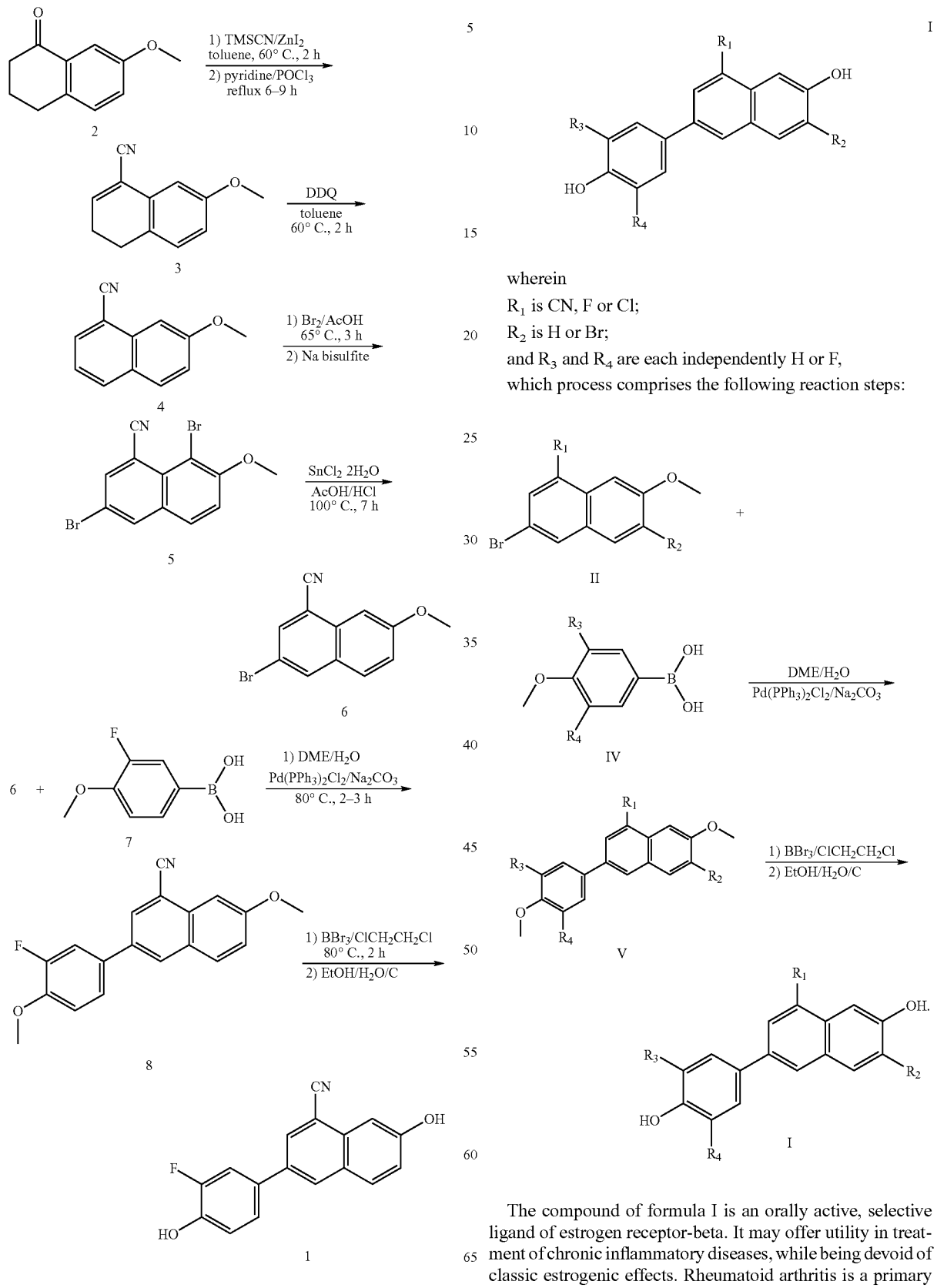

In a broader aspect of the present invention, there is provided a process for preparing a compound of formula I wherein
R$_1$ is CN, F or Cl;
R$_2$ is H or Br;
and R$_3$ and R$_4$ are each independently H or F,
which process comprises the following reaction steps:

The compound of formula I is an orally active, selective ligand of estrogen receptor-beta. It may offer utility in treatment of chronic inflammatory diseases, while being devoid of classic estrogenic effects. Rheumatoid arthritis is a primary therapeutic indication for the compound.

In a preferred aspect of the present invention, the compound of formula II is obtained by heating the compound of formula III

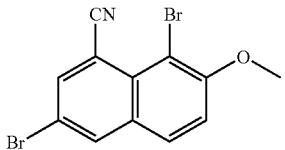

with stannous chloride in a mixture of acetic acid and concentrated hydrochloric acid, most preferably at a temperature of about 100° C. until the reaction reaches completion. The compound of formula III is novel, and the route through this compound in the process of the present invention provides a very efficient method for producing compounds of formulae I and II in which $R_1$=CN and $R_2$=H in relatively high purity, compared to known synthetic methods.

According to a preferred process of the present invention, the compound of formula III is formed by dibrominating 7-methoxy-1-naphthonitrile, preferably using bromine in acetic acid at a temperature not exceeding about 70° C., preferably at a temperature in the approximate range of 40-70° C., most preferably at about 65° C. Upon the completion of the reaction, the reaction mixture is quenched with sodium bisulfite to reduce excess bromine. The formula III compound precipitates with a surprisingly high yield (typically about 90-95%) and purity (typically about 93-95%). Advantageously, this high purity allows this compound to be used to make the compound of formula II without further purification steps.

Another novel aspect of the present invention is the highly efficient manner in which the compound 7-methoxy-1-naphthonitrile is provided starting from 7-methoxy-1-tetralone (3,4-dihydro-7-methoxy-1(2H)-naphthalenone) without isolating the intermediate unsaturated nitrile. An especially novel aspect of this process is the use of DDQ, preferably in toluene at temperatures in the approximate range of 40-80° C., more preferably at about 50-70° C., and most preferably at about 60° C., to convert the unsaturated nitrile intermediate to the 7-methoxy-1-naphthonitrile in relatively high yield.

Pharmaceutical acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable aids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1-6 carbon atoms ordialkylammonium salts containing 1-6 carbon atoms in each alkyl group, and trialkylammonium salts containing 1-6 carbon atoms in each alkyl group, when a compound of this invention contains an acidic moiety.

Pharmaceutically acceptable esters include those formed by reaction with $C_1$-$C_6$ alkanoic acids.

The following examples are presented to illustrate certain embodiments of the present invention, but should not be construed as limiting the scope of this invention.

EXAMPLE 1

7-METHOXY-1-NAPHTHONITRILE

To solution of 3,4-dihydro-7-methoxy-1(2H)-naphthalenone (200 g, 1.14 mol) and zinc iodide (9.09 g, 0.0285 mol) in toluene (600 mL) at 45° C. is added trimethylsilyl cyanide (120 g, 1.21 mol) during a period of 20 min. The mixture is heated to 60° C. and stirred for 2 h. The mixture is cooled to 35° C. and pyridine (79.1 g, 1.71 mol) and phosphorus oxychloride (262 g, 1.71 mol) were added respectively. The mixture is heated to 100° C. and stirred for 6 h. The reaction mixture is cooled to 50° C. and added to a pre-cooled sodium hydroxide solution (3N, 2 L, 3° C.) during a period of 15 min. Toluene (1.2 L) is added and the mixture is cooled to room temperature. The organic phase is separated and wished with sodium hydroxide solution (1 N, 2×1 L), water (1 L), hydrochloride acid (3 N, 3×1 L), water (1 L), saturated sodium bicarbonate solution (1 L) and brine (1 L) respectively.

The organic layer is heated to 45° C. and 2,3-dichloro-5,6-dicyano-1,4-benzoquinone (DDQ) (207 g, 0.912 mol) is added in portions during a period of 20 min. The mixture is heated to 60° C. and stirred for 2 h and then cooled to room temperature. The solid is removed by filtration and the filtrate is washed with sodium hydroxide solution (2×0.8 L) and brine (0.8 L) respectively. Most of the solvent is removed by distillation and heptane (1 L) is added. The solid is filtered at 0° C. and dried to give the title compound (white solid, 130 g, 73%). $^1$H NMR (CDCl$_3$): δ 8.00 (d, 1H, J=8.2 Hz), 7.94 (dd, 1H, J=1.1 Hz, 7.3 Hz), 7.81 (d, 1H, J=8.9 Hz), δ 7.47 (d, 1H, J=2.4 Hz), 7.38 (dd, 1H, J=7.9 Hz, 8.0 Hz), 7.26 (dd, 1H, J=2.4 Hz, 8.9 Hz), 4.00 (s, 3H).

EXAMPLE 2

3,8-DIBROMO-7-METHOXY-1-NAPHTHONITRILE

To slurry of 7-methoxy-1-naphthonitrile (500 g, 2.73 mol) in acetic acid (5 L) is added bromine (2.55 kg, 16.0 mol) at 40 to 55° C. during a period of 15 min. Then, the mixture is heated to 65° C. and stirred for 3 h. The mixture is cooled to room temperature. A solution of sodium bisulfite (1.3 kg) in water (3.0 L) is added during a period of 60 min while maintaining the reaction temperature below 40° C. The solid is filtered and washed with water (4×2.5 L). A small amount of the sample is dried and analyzed. The rest of wet product is used directly for the reaction of Example 3, below. The dried compound is a white solid. $^1$H NMR (CDCl$_3$): δ 8.15 (d, 1H, J=2.1 Hz), 8.10 (d, 1H, J=2.1 Hz), 7.81 (d, 1H, J=9.1 Hz), 7.38 (d, 1H, J=9.1 Hz), 4.06 (s, 3H).

EXAMPLE 3

3-BROMO-7-METHOXY-1-NAPHTHONITRILE

To slurry of 3,8-dibromo-7-methoxy-1-naphthonitrile (1.62 kg) and Tin (II) chloride dihydrate (1.24 kg, 5.50 mol) in acetic acid (5 L) is added conc. HCl (37% wt, 2.50 L) through a dropping funnel at 100° C. during a period of 2 h. The mixture is stirred at 100° C. for 4 h. Then, the mixture is cooled to room temperature. The solid is filtered, washed with 1% wt HCl (2×1.00 L), water (1.00 L) and dried to give the title compound as a white solid (524 g, 73%). $^1$H NMR (CDCl$_3$): δ8.13 (d, 1H, J=1.8 Hz), 7.93 (d, 1H, J=1.9 Hz), 7.72 (d, 1H, J=9.0 Hz), 7.41 (d, 1H, J=2.4 Hz), 7.28 (dd, 1H, J=2.4 Hz, 9.0 Hz), 3.99 (s, 3H).

EXAMPLE 4

3-(3-FLUORO-4-METHOXYPHENYL)-7-MEY-THOXY-1-NAPHTHONITRILE

A mixture of 3-bromo-7-methoxy-1-naphthonitrile (100 g, 0.382 mol), sodium carbonate (121 g, 1.15 mol), dichlorobis(triphenylphosphine) palladium (II) (0.27 g, 0.0004 mol), 3-fluoro-4-methoxyphenylboronic acid (71.3 g, 0.420 mol), water (600 mL) and 1,2-dimethoxyethane (1000 mL) is heated to 80° C. and stirred for 2 h, then water (600 mL) is added. The mixture is cooled to room temperature. The solid is filtered and washed with water (2×200 mL) and dried to produce the title compound as a white solid (118 g, 98%). $^1$H NMR (CDCl$_3$): δ 8.10 (d, 1H, J=1.6 Hz), 8.06 (d, 1 H, J=1.9 Hz), 7.84 (d, 1H, J=9.0 Hz), 7.27-7.47 (m, 4H), 7.08 (t, 1H, J=8.4 Hz), 4.01 (s, 3H), 3.96 (s, 3H).

EXAMPLE 5

3-(3-FLUORO-4-HYDROXYPHENYL)-7-HY-DROXY-1-NAPHTHONITRILE

To slurry of 3-(3-fluoro-4-methoxyphenyl)-7-meythoxy-1-naphthonitrile (200 g, 0.651 mol) in 1,2-dichloroethane (2000 mL) is added BBr$_3$ (511 g, 2.04 mol) during a period of 20 min, while keep the reaction temperature below 40° C. Then the mixture is heated to 83° C. and stirred for 4 h. The reaction mixture is cooled to 3° C. and added to a cold water (2000 mL) during a period of 20 min. The solid is filtered and washed with 0.5 N HCl (4×1000 mL), water (1000 mL) and cold ethanol (400 mL) and dried to give a crude product which can be recrystallized from ethanol and water to provide the title compound as a pale yellow solid (174 g, 96%). $^1$H NMR (DMSO$_{d6}$): δ 10.48 (s, 1H), 10.10 (s, 1H), 8.44 (s, 1H), 8.37 (d, 1H, J=1.8 Hz), 8.01 (d, 1H, J=9.0 Hz), 7.71 (dd, 1H, J=2.1 Hz, 10.8 Hz), 7.52 (dd, 1H, J=2.1 Hz, 8.4 Hz), 7.36 (d, 1H, J=2.1 Hz), 7.26 (dd, 1H, J=2.1 Hz, 8.7 Hz), 7.07 (t, 1H, J=9.0 Hz).

Many variations of the present invention not illustrated herein will occur to those skilled in the art. The present invention is not limited to the embodiments illustrated and described herein, but encompasses all the subject matter within the scope of the appended claims.

What is claimed is:

1. A process for making a compound of formula I

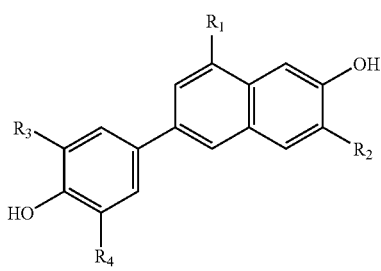

I wherein
R$_1$ is CN, F or Cl;
R$_2$ is H or Br;
and R$_3$ and R$_4$ are each independently H or F,
said process comprising the steps of:
a) reacting a compound of formula II

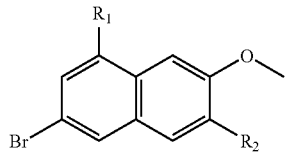

II wherein R$_1$ and R$_2$ are as defined above, with a compound of formula IV

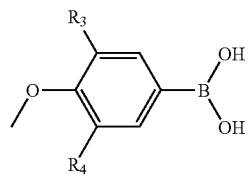

IV wherein R$_3$ and R$_4$ are as defined above, in the presence of Pd(PPh$_3$)$_2$Cl$_2$ to obtain a compound of formula V

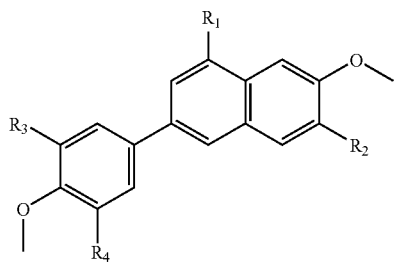

V b) converting the compound of formula V to a compound of formula I.

2. The process of claim 1 wherein R$_1$ is CN.
3. The process of claim 2 wherein R$_2$ is H.
4. The process of claim 1 wherein R$_3$ is F.
5. The process of claim 4 wherein R$_4$ is H.
6. The process of claim 4 wherein R$_1$ is CN and R$_2$ is H.
7. The process of claim 1, wherein the step of reacting a compound of formula II with a compound of formula IV is conducted in DME/water in the presence of Na$_2$CO$_3$.
8. The process of claim 1, wherein the step of converting a compound of formula V to a compound of formula I is accomplished by reaction with BBr$_3$.
9. The process of claim 8, wherein the conversion of the compound of formula V to a compound of formula I is accomplished by reaction with BBr$_3$ in ClCH$_2$CH$_2$Cl, followed by treatment with EtOH/H$_2$O/C.
10. The process of claim 5 wherein R$_1$ is CN and R$_2$ is H.

* * * * *